Sept. 17, 1940. F. L. STURM Plant Pat. 424
GERANIUM PLANT
Filed May 20, 1940
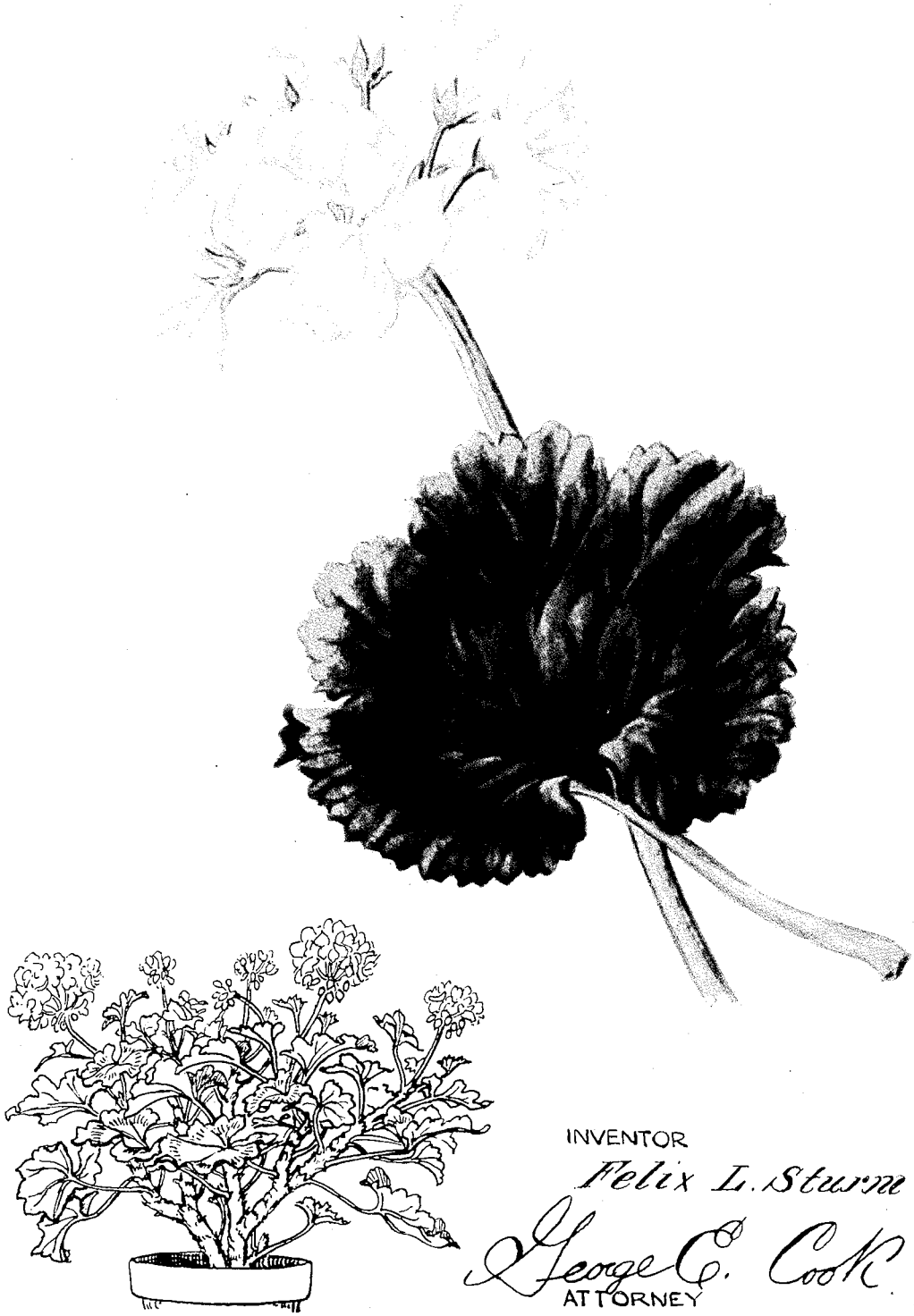
INVENTOR
Felix L. Sturm
George C. Cook
ATTORNEY Patented Sept. 17, 1940

Plant Pat. 424

UNITED STATES PATENT OFFICE

424

GERANIUM PLANT

Felix L. Sturm, Shinnston, W. Va.

Application May 20, 1940, Serial No. 336,305

1 Claim. (Cl. 47—60)

My present discovery relates to a new and improved variety of geranium, its novelty pertaining primarily to color but including other useful improvements also. The flower of this new variety is a vivid begonia rose color not found in the flower of any other geranium known to me.

The new variety was discovered by me in my greenhouses, growing as a sport branch on a plant of the variety Fiat. For several years this variety has been reproduced asexually and the best specimens saved to produce the succeeding generation. By this method of selection and reproduction the outstanding and desirable features of the sport have been preserved. Of the thousand or so plants produced last year, not more than three or four were discarded.

Like its parent, this new variety is an excellent type of geranium for potting and window boxes, because of its compact, dwarf growth which is at the same time very sturdy and vigorous. Its large, evenly-shaped flower clusters are carried on short, heavy stems, and the foliage is very heavy and dark. The strong flower stems do not break easily in the wind.

A distinctive feature is its habit of blooming freely all winter as well as in the summer, either in the greenhouse or in the home. No other variety known to me has this continuous blooming habit throughout the year. It is very prolific in production of blossoms, a single plant having as many as twelve nice clusters at one time.

Distinctive also is the fact that the blossoms of this variety fall less readily than those of any other variety known to me. This feature is valuable because it enables the plants to be handled with much less destruction to the blossoms than is usually the case.

Although blossoms of the parent are single, most of the blossoms of this variety have two rows of petals, the inner row being of smaller petals than the outer row. Few geraniums have this feature of doubleness of blossoms.

The original illustrations accompanying this application show a cluster of the blossoms and a leaf in full color, and a black-and-white drawing indicating the compact growth of the plant.

Following is a description of the flower and plant of this variety of geranium. Color names refer to Ridgeway's Color Standards and Nomenclature, except where the dictionary term is obviously intended.

*The plant*

Growth—Bushy; compact; medium in height, with tendency to dwarfness.

Disease resistance—Good.

Blooming habit—Continuous; exceedingly prolific.

Inflorescence—Umbel; large; compact.

Foliage:

*Size*—Large; leaf average is 4 to 5 inches across when grown in pot, although often 6+ inches is attained.

*Color*—Dark green with darker and clearly defined marginal zone. Approximately Forest Green (Plate XVII) in center, with marginal region approximately Hellebore Green (Plate XVII). The under surface is Cress Green (Plate XXXI).

*Shape*—Disk-shaped, with lobulated margin.

*Edge*—Serrately lobed; wavy.

*Texture*—Heavy; surface soft and fuzzy.

Stem—Short; heavy; fuzzy; very strong; Rainette Green (Plate XXXI).

Peduncle—Strong and heavy; Rainette Green with occasional bronze overlay; able to resist most winds and thereby avoid breakage.

*The flower*

Bud:

*Calyx*—Consists of 5 separated sepals.

*Sepals*—Long; pointed; hairy on outer surface, smooth on inner surface; Rainette Green (Plate XXXI).

*Pedicels*—Strong; 1 to 1¼ inches in length.

*Size*—Normal.

*Color*—Begonia Rose (Plate I).

*Form*—Ovoid.

*Opening*—Opens well; little affected by weather.

Florets:

*Size*—1¼ to 1½ inches across.

*Petalage*—Usually double, with 8 to 10 petals.

*Color*—Between Eosine Pink and Begonia Rose (Plate I).

*Fragrance*—Very mild.

*Lasting quality*—Excellent; petals cling tenaciously.

*Discoloration*—None.

*Petals:*

*Texture*—Very substantial.

*Shape*—Obovate; margins entire.

*Size*—¾ inch long by ⅝ inch wide.

Reproductive organs:

*Stamens*—Anthers large; cream-yellow. Filaments flat; white; medium length; number about seven.

*Pistils*—Styles 3 to 5. Stigmas 3 to 5; red.

*Ovary*—Long; fuzzy at top, feathery at base; light green.

Having thus disclosed my discovery, I claim:

A new and distinct variety of geranium plant with features in combination substantially as shown and described, characterized particularly by its compact, dwarf growth; its strong, heavy flower stems; its heavy, dark foliage; its continuous blooming habit the year round; and its prolific production of large clusters of blossoms of distinctive Eosine Pink to Begonia Rose color, which are usually double and the petals of which cling unusually well.

FELIX L. STURM.